(12) United States Patent
Bae et al.

(10) Patent No.: US 12,207,907 B2
(45) Date of Patent: Jan. 28, 2025

(54) APPARATUS AND METHOD FOR ESTIMATING BLOOD PRESSURE

(71) Applicants: SAMSUNG ELECTRONICS CO., LTD., Suwon-si (KR); IUCF-HYU (Industry-University Cooperation Foundation Hanyang University), Seoul (KR)

(72) Inventors: Sang Kon Bae, Seongnam-si (KR); Joon-Hyuk Chang, Seoul (KR); Chang Mok Choi, Suwon-si (KR); Youn Ho Kim, Hwaseong-si (KR); Jin Woo Choi, Suwon-si (KR); Jehyun Kyung, Seoul (KR); Tae-Jun Park, Seoul (KR); Joon-Young Yang, Seoul (KR); Inmo Yeon, Seoul (KR)

(73) Assignees: SAMSUNG ELECTRONICS CO., LTD., Suwon-si (KR); IUCF-HYU (INDUSTRY-UNIVERSITY COOPERATION FOUNDATION HANYANG UNIVERSITY), Seoul (KR)

( * ) Notice: Subject to any disclaimer, the term of this patent is extended or adjusted under 35 U.S.C. 154(b) by 1112 days.

(21) Appl. No.: 17/097,625

(22) Filed: Nov. 13, 2020

(65) Prior Publication Data
US 2022/0015651 A1    Jan. 20, 2022

(30) Foreign Application Priority Data
Jul. 16, 2020  (KR) .................. 10-2020-0088178

(51) Int. Cl.
*A61B 5/022*  (2006.01)
*A61B 5/00*  (2006.01)
*A61B 5/021*  (2006.01)

(52) U.S. Cl.
CPC ...... *A61B 5/02225* (2013.01); *A61B 5/02116* (2013.01); *A61B 5/7267* (2013.01)

(58) Field of Classification Search
None
See application file for complete search history.

(56) References Cited

U.S. PATENT DOCUMENTS 9,924,870 B2  3/2018  Visvanathan et al.
10,417,563 B1  9/2019  Commons et al.
(Continued)

FOREIGN PATENT DOCUMENTS

KR    10-1803471 B1    12/2017
KR    10-1820511 B1    1/2018
(Continued)

OTHER PUBLICATIONS

English Translation of WO 2019216417A1, Sharp Corporation, 15 pages, printed on May 4, 2024,. (Year: 2019).*

*Primary Examiner* — Matthew Kremer
*Assistant Examiner* — Jennifer Grace Baires-Tweed
(74) *Attorney, Agent, or Firm* — Sughrue Mion, PLLC

(57) ABSTRACT

An apparatus for and a method for estimating blood pressure are provided. The apparatus for estimating blood pressure includes: a sensor configured to measure a pulse wave signal from an object; and a processor configured to obtain a mean arterial pressure (MAP) based on the pulse wave signal, configured to classify a phase of the obtained MAP according to at least one classification criterion, and to obtain a systolic blood pressure (SBP) by using an estimation model corresponding to the classified phase of the MAP among estimation models corresponding to respective phases of the MAP.

10 Claims, 14 Drawing Sheets

(56) References Cited

U.S. PATENT DOCUMENTS

| | | | | |
|---|---|---|---|---|
| 2016/0166160 A1* | 6/2016 | Casale | ................ | A61B 5/0295 |
| | | | | 600/480 |
| 2018/0132731 A1* | 5/2018 | Albadawi | ............ | A61B 5/7267 |
| 2018/0235487 A1* | 8/2018 | Paul | ................... | A61B 5/02416 |
| 2019/0142286 A1 | 5/2019 | Mouradian | | |
| 2021/0193311 A1* | 6/2021 | Addison | .............. | A61B 5/7267 |

FOREIGN PATENT DOCUMENTS

| | | | | |
|---|---|---|---|---|
| KR | 10-2019-0061446 A | 6/2019 | | |
| KR | 10-1998950 B1 | 7/2019 | | |
| KR | 10-2018346 B1 | 10/2019 | | |
| KR | 10-2042700 B1 | 11/2019 | | |
| WO | WO-2019060671 A1 * | 3/2019 | ......... | A61B 5/02108 |
| WO | WO-2019216417 A1 * | 11/2019 | ........... | A61B 5/0059 |
| WO | 2020/009387 A1 | 1/2020 | | |

\* cited by examiner

APPARATUS AND METHOD FOR ESTIMATING BLOOD PRESSURE

CROSS-REFERENCE TO RELATED APPLICATION(S)

This application claims priority from Korean Patent Application No. 10-2020-0088178, filed on Jul. 16, 2020, in the Korean Intellectual Property Office, the entire disclosure of which is herein incorporated by reference for all purposes.

BACKGROUND

1. Field

Example embodiments of the disclosure relate to technology for cuffless blood pressure estimation, and more particularly to, an apparatus and a method for estimating blood pressure based on deep learning.

2. Description of the Related Art

Generally, methods of non-invasively measuring blood pressure without damaging a human body include a method to measure blood pressure by measuring a cuff-based pressure and a method to estimate blood pressure by measuring pulse waves without the use of a cuff. A Korotkoff-sound method is one of cuff-based blood pressure measurement methods, in which a pressure in a cuff wound around an upper arm is increased and blood pressure is measured by listening to the sound generated in the blood vessel through a stethoscope while decreasing the pressure. Another cuff-based blood pressure measurement method is an oscillometric method using an automated machine, in which a cuff is wound around an upper arm, a pressure in the cuff is increased, a pressure in the cuff is continuously measured while the cuff pressure is gradually decreased, and blood pressure is measured based on a point where a change in a pressure signal is large. Cuffless blood pressure measurement methods generally include a method of estimating blood pressure by calculating a Pulse Transit Time (PTT), and a Pulse Wave Analysis (PWA) method of estimating blood pressure by analyzing a pulse wave shape.

SUMMARY

In accordance with an aspect of an example embodiment, there is provided an apparatus for estimating blood pressure, the apparatus including: a sensor configured to measure a pulse wave signal from an object; and a processor configured to obtain a mean arterial pressure (MAP) based on the pulse wave signal, configured to classify a phase of the obtained MAP according to at least one classification criterion, and to obtain a systolic blood pressure (SBP) by using an estimation model corresponding to the classified phase of the MAP among estimation models corresponding to respective phases of the MAP.

The processor may be further configured to obtain the SBP by using the estimation model, the estimation model being trained based on deep learning, including Deep Neural Network (DNN), and generated for the classified phase of the MAP that is defined based on a magnitude of the MAP.

The processor may be further configured to extract a feature based on the pulse wave signal, and obtain an initial SBP and an initial diastolic blood pressure (DBP) from the extracted feature by using an initial estimation model.

The sensor may be further configured to measure a contact force applied by the object to the sensor, and the processor may be further configured to obtain an oscillometric waveform envelope based on the pulse wave signal and the contact force, and extract the feature based on the obtained oscillometric waveform envelope.

The processor may be further configured to extract as the feature, from the oscillometric waveform envelope, one or more of a maximum amplitude value, a contact pressure value at a maximum amplitude point, a width between points corresponding to a predetermined percentage of the maximum amplitude value, and a contact pressure value at a point corresponding to an amplitude value which is the predetermined percentage of the maximum amplitude value.

The processor may be further configured to: obtain the MAP based on the initial SBP and the initial DBP; and obtain the SBP by inputting the initial SBP and the extracted feature to the estimation model.

The processor may be further configured to obtain a first MAP based on the initial SBP and the initial DBP, obtain a first SBP by using a first estimation model corresponding to a phase of the first MAP among first estimation models corresponding to respective phases of the first MAP, obtain a second MAP based on the obtained first SBP and the initial DBP, and obtain a second SPB by using a second estimation model corresponding to a phase of the second MAP among second estimation models corresponding to respective phases of the second MAP.

The processor may be further configured to: obtain the first SBP by inputting the initial SBP and the feature to the first estimation model; and obtain the second SBP by inputting the first SBP and the feature to the second estimation model.

In accordance with an aspect of an example embodiment, there is provided an apparatus for estimating blood pressure, the apparatus including: a sensor configured to measure a pulse wave signal from an object; and a processor configured to extract a feature based on the pulse wave signal, to classify a phase of a mean arterial pressure (MAP) based on the extracted feature by using two or more classifiers, and to obtain an SBP by using an estimation model corresponding to the classified phase of the MAP among estimation models corresponding to respective phases of the MAP.

The processor may be further configured to input the extracted feature into a first classifier, and in response to an output value of the first classifier exceeding a first threshold value, classify the MAP as a first phase.

In response to the output value of the first classifier being less than or equal to the first threshold value, the processor may be further configured to input the feature into a second classifier, and in response to an output value of the second classifier exceeding a second threshold value, classify the MAP as the first phase.

The processor may be further configured to input the extracted feature into a third classifier, and in response to an output value of the third classifier exceeding a third threshold value, classify the MAP as a third phase, and in response to the output value of the second classifier being less than or equal to the second threshold value and the output value of the third classifier being less than or equal to the third threshold value, classify the MAP as a second phase.

The first threshold value, the second threshold value, and the third threshold value may be respectively obtained by training the first classifier, the second classifier, and the third classifier based on deep learning using training data, the training data including a plurality of features extracted based on pulse wave signals.

The processor may be further configured to obtain an initial SBP from the extracted feature by using an initial estimation model, and obtain the SBP by inputting the feature and the initial SBP to the estimation model.

In accordance with an aspect of an example embodiment, there is provided a method of estimating blood pressure, the method including: measuring a pulse wave signal from an object; obtaining a mean arterial pressure (MAP) based on the pulse wave signal, and classifying a phase of the obtained MAP according to at least one classification criterion; and obtaining SBP by using an estimation model corresponding to the classified phase of the MAP among estimation models corresponding to respective phases of the MAP.

The method may further include extracting a feature based on the pulse wave signal; and obtaining an initial SBP and an initial DBP from the extracted feature by using an initial estimation model.

The method may further include measuring a contact force applied by the object to a pulse wave sensor, the pulse wave sensor configured to measure the pulse wave signal from the object, wherein the extracting includes obtaining an oscillometric waveform envelope based on the pulse wave signal and the contact force, and extracting the feature based on the obtained oscillometric waveform envelope.

The classifying may include obtaining the MAP based on the initial SBP and the initial DBP, and the obtaining the SBP may include obtaining the SBP by inputting the initial SBP and the extracted feature to the estimation model.

The classifying may include: obtaining a first MAP based on the initial SBP and the initial DBP; classifying a phase of the first MAP according to a first classification criterion; obtaining a first SBP by using a first estimation model corresponding to the phase of the first MAP among first estimation models for respective phases of the first MAP; obtaining a second MAP based on the first SBP and the initial DBP; and classifying a phase of the second MAP according to a second classification criterion.

The obtaining the SBP may include obtaining a second SBP by inputting the first SBP and the feature to a second estimation model corresponding to the phase of the second MAP.

BRIEF DESCRIPTION OF THE DRAWINGS

To describe the technical solutions in the embodiments of the disclosure more clearly, the following briefly describes the accompanying drawings required for describing the embodiments of the disclosure.

DETAILED DESCRIPTION

Figure 1:
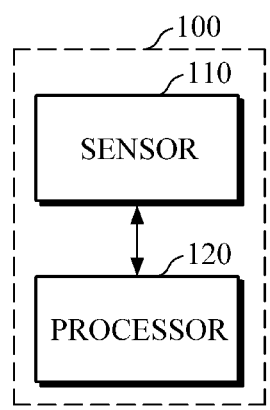
FIG. 1 is a block diagram illustrating an apparatus for estimating blood pressure according to an example embodiment of the disclosure.

Details of example embodiments are included in the following detailed description and drawings. Advantages and features of the disclosure, and a method of achieving the same will be more clearly understood from the following embodiments described in detail with reference to the accompanying drawings. Throughout the drawings and the detailed description, unless otherwise described, the same drawing reference numerals will be understood to refer to the same elements, features, and structures.

It will be understood that, although the terms first, second, etc. may be used herein to describe various elements, these elements should not be limited by these terms. These terms are only used to distinguish one element from another. Also, the singular forms are intended to include the plural forms as well, unless the context clearly indicates otherwise. It will be further understood that when an element is referred to as "comprising" another element, the element is intended not to exclude one or more other elements, but to further include one or more other elements, unless explicitly described to the contrary. In the following description, terms such as "unit" and "module" indicate a unit for processing at least one function or operation and they may be implemented by using hardware, software, or a combination thereof.

Hereinafter, example embodiments of an apparatus and method for estimating blood pressure will be described in detail with reference to the accompanying drawings.

FIG. 1 is a block diagram illustrating an apparatus for estimating blood pressure according to an example embodiment of the disclosure.

Referring to FIG. 1, an apparatus 100 for estimating blood pressure includes a sensor 110 and a processor 120.

The sensor 110 may include a pulse wave sensor for measuring a pulse wave signal, including a photoplethysmography (PPG) signal, when an object is in contact with the pulse wave sensor. The object may be a body part, which may come into contact with the pulse wave sensor, and at which pulse waves may be easily measured. For example, the object may be a finger where blood vessels are densely located, but the object is not limited thereto and may be an area on a wrist that is adjacent to the radial artery, or a peripheral part of the body, such as an upper portion of the wrist, toes, etc., where veins or capillaries are located.

The pulse wave sensor may include one or more light sources for emitting light onto the object, and one or more detectors which are disposed at positions spaced apart from the one or more light sources by a predetermined distance and detect light scattered or reflected from the object. The one or more light sources may emit light of different wavelengths. For example, the one or more light sources may emit light of an infrared wavelength, a green wavelength, a blue wavelength, a red wavelength, a white wavelength, and the like. The one or more light sources may include a light emitting diode (LED), a laser diode (LD), a phosphor, etc., but are not limited thereto. Further, the one or more detectors may include a photodiode, a photodiode array, a complementary metal-oxide semiconductor (CMOS) image sensor, a charge-coupled device (CCD) image sensor, and the like.

Further, the sensor 110 may include a force/pressure sensor (or a force and/or pressure sensor). When a user places an object on the pulse wave sensor and increases or decreases pressure to induce a change in pulse wave amplitude, the force/pressure sensor may measure a contact force/pressure exerted between the pulse wave sensor and the object. The force/pressure sensor may include a force sensor including a strain gauge and the like, a force sensor array, a pressure sensor, an air bladder type pressure sensor, a pressure sensor in combination with a force sensor and an area sensor, and the like.

The processor 120 may estimate blood pressure based on the pulse wave signal measured by the sensor 110. For example, the processor 120 may obtain mean arterial pressure (MAP) based on the pulse wave signal, may select an estimation model based on the obtained MAP, and may estimate blood pressure by using the selected estimation model. The blood pressure estimation model may be trained based on deep learning, including Deep Neural Network (DNN), and may be pre-generated for each of phases classified according to magnitudes of MAP.

In embodiments of the disclosure, the MAP is divided into, for example, three phases of high, medium, and low according to magnitudes of the MAP, and the blood pressure estimation model is trained and generated for each phase and is used for estimating blood pressure, such that the accuracy of blood pressure estimation may be further improved.

Figure 2:
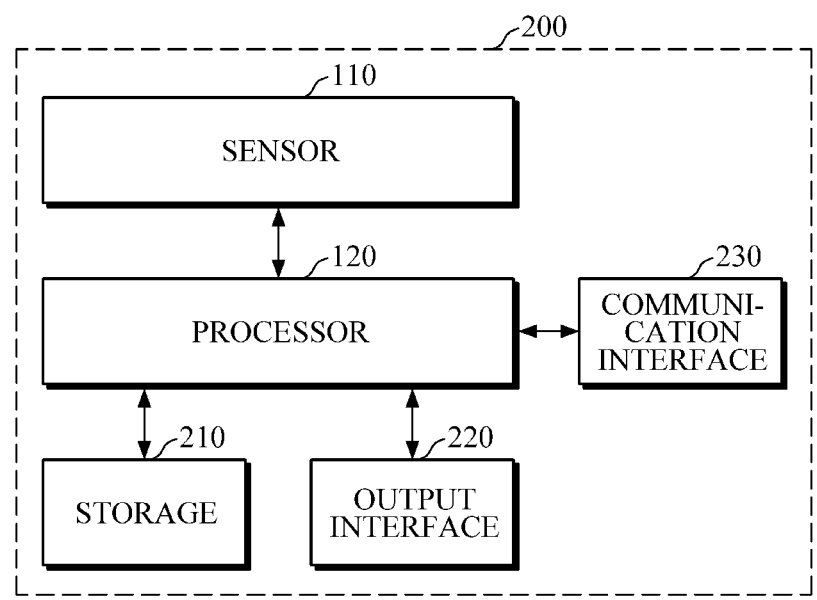
FIG. 2 is a block diagram illustrating an apparatus for estimating blood pressure according to another example embodiment of the disclosure.

FIG. 2 is a block diagram illustrating an apparatus for estimating blood pressure according to another example embodiment of the disclosure.

Referring to FIG. 2, an apparatus 200 for estimating blood pressure according to another example embodiment includes the sensor 110, the processor 120, a storage 210, an outputter 220, and a communicator 230. The sensor 110 and the processor 120 are similar to those described above.

The storage 210 may store information related to estimating blood pressure. For example, the storage 210 may store pulse wave signals, contact force/pressure values, estimated blood pressure values, and the like. Further, the storage 210 may store a blood pressure estimation model for each phase, an initial estimation model, phase classification criteria, user characteristic information, and the like. The user characteristic information may include a user's age, gender, health condition, and the like.

The storage 210 may include at least one storage medium among a flash memory type memory, a hard disk type memory, a multimedia card micro type memory, a card type memory (e.g., an SD memory, an XD memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like, but is not limited thereto.

The outputter 220 may provide processing results of the processor 120. For example, the outputter 220 may display an estimated blood pressure value of the processor 120 on a display. If the estimated blood pressure value falls outside a normal range, the outputter 220 may provide a user with warning information by changing color, line thickness, etc., or displaying the abnormal value along with a normal range, so that the user may easily recognize the abnormal value. Further, along with or alternatively to the visual output, the outputter 220 may output a blood pressure estimation result in a non-visual manner by voice, vibrations, tactile sensation, and the like using a voice output module such as a speaker, or a haptic module and the like.

The communicator 230 may communicate with an external device to transmit and receive various data, related to estimating blood pressure, to and from the external device. The external device may include an information processing device such as a smartphone, a tablet PC, a desktop computer, a laptop computer, and the like. For example, the communicator 230 may transmit a blood pressure estimation result to a user's smartphone and the like, so that the user may manage and monitor the blood pressure estimation result by using a device having a relatively high performance. Further, the external device may include an external blood pressure estimating device for generating a blood pressure estimation model, and upon receiving the blood pressure estimation model from the external blood pressure estimating device, the communicator 230 may store the blood pressure estimation model in the storage 210.

The communicator 230 may communicate with the external device by using various wired or wireless communication techniques, such as Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WIFI communication, Radio Frequency Identification (RFID) communication, 3G communication, 4G communication, 5G communication, and the like. However, this is merely an example and is not intended to be limiting.

Figure 3:
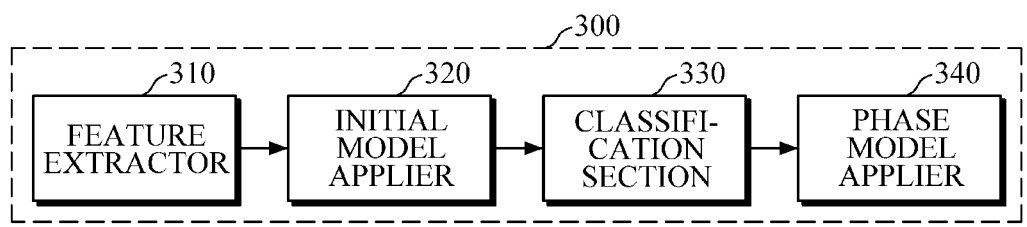
FIG. 3 is a diagram illustrating an example of a configuration of a processor of FIGS. 1 and 2.
Figure 4A:
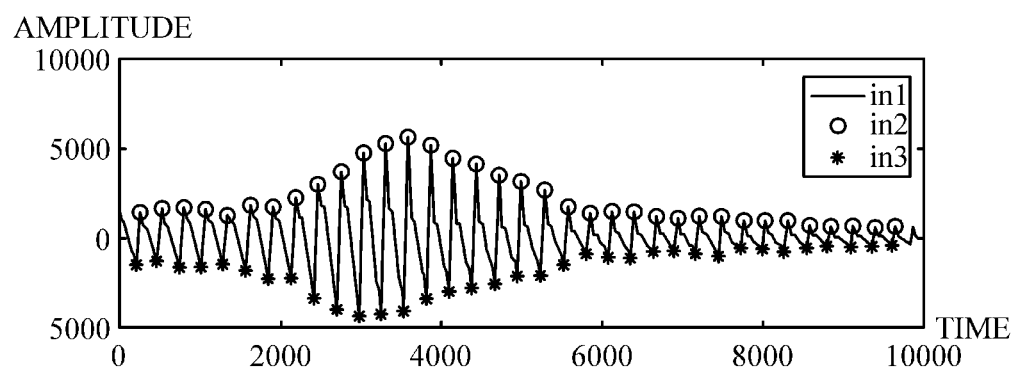
FIGS. 4A and 4B are diagrams explaining an example of estimating blood pressure using oscillometry.
Figure 4B:
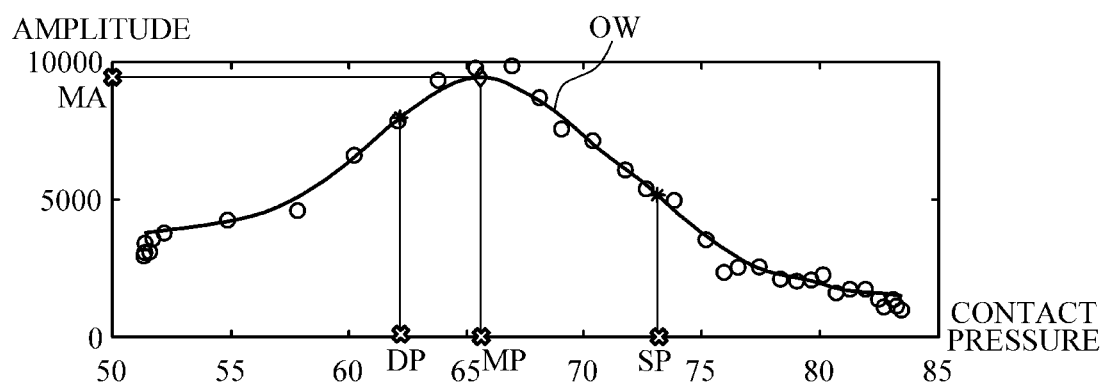

FIG. 3 is a diagram illustrating an example of a configuration of a processor of FIGS. 1 and 2. FIGS. 4A and 4B are diagrams explaining an example of estimating blood pressure using oscillometry.

Referring to FIG. 3, the processor 300 according to an embodiment includes a feature extractor 310, an initial model applier 320, a classification section 330, and a phase model applier 340.

The feature extractor 310 may extract features based on a pulse wave signal measured by the sensor 110.

For example, by analyzing a waveform of the pulse wave signal, the feature extractor 310 may extract features including, for example, amplitude and/or time values at a maximum point of the pulse wave, time and amplitude values of constituent pulse waveform components related to propagation and reflection waves, an area of a predetermined period of a waveform of the pulse wave signal, and the like.

Further, the feature extractor 310 may generate an oscillometric waveform envelope based on the pulse wave signal and the contact force/pressure, which are measured by the sensor 110, and may extract features based on the oscillometric waveform envelope.

For example, referring to FIGS. 4A and 4B, the feature extractor 310 may extract, e.g., a peak-to-peak point of the pulse wave signal waveform by subtracting a negative (−) amplitude value in3 from a positive (+) amplitude value in2 of a waveform envelope in1 at each measurement time of the pulse wave signal. In addition, the feature extractor 310 may obtain an oscillometric waveform envelope OW by plotting the peak-to-peak amplitude at each measurement time against the contact pressure value at a corresponding time and by performing, for example, polynomial curve fitting.

The feature extractor 310 may extract features by using the generated oscillometric waveform envelope OW. For example, the feature extractor 310 may extract features, from the oscillometric waveform envelope OW, including an amplitude value MA at a maximum point of the pulse wave, a contact pressure value MP at the maximum point of the pulse wave, a contact pressure value DP at a point corresponding to an amplitude value which is a first percentage of the amplitude value MA at the maximum point, a contact pressure value SP at a point corresponding to an amplitude value which is a second percentage of the amplitude value MA at the maximum point, a width between points corresponding to a predetermined percentage (e.g., 50%, 70%, etc.) of an interval between an onset point and a maximum point of the pulse wave in the oscillometric waveform envelope OW, and the like.

Further, the feature extractor 310 may extract user characteristic information, e.g., a user's age, gender, health condition, etc., as features from the storage 210.

The initial model applier 320 may obtain an initial systolic blood pressure (SBP) and/or an initial diastolic blood pressure (DBP) from the features, extracted by the feature extractor 310, by using a pre-defined initial estimation model. The initial estimation model may include an SBP estimation model based on DNN and a DBP estimation model based on DNN, and may be pre-generated by being trained based on deep learning using the aforementioned features as training data.

The classification section 330 may obtain MAP based on the initial systolic blood pressure (SBP) and the initial diastolic blood pressure (DBP) which are obtained by the initial model applier 320. For example, the classification section 330 may obtain MAP by using the following Equation 1, in which PP denotes pulse pressure. However, the classification section 330 is not limited thereto.

$$DBP = MAP - \frac{PP}{3}$$
$$SBP = DBP + PP$$
$$MAP = \frac{1}{3}SBP + \frac{2}{3}DBP$$

[Equation 1]

Upon obtaining the MAP, the classification section 330 may classify phases of the MAP according to pre-defined classification criteria. For example, the classification criteria are defined in such a manner that if the MAP is greater than or equal to a first value (e.g., 95), the classification section 330 may classify the MAP as a first phase, if the MAP is less than the first value but greater than a second value (e.g., 75), the classification section 330 may classify the MAP as a second phase, and if the MAP is less than or equal to the second value, the classification section 330 may classify the MAP as a third phase. However, the classification criteria are not limited thereto, and the MAP may be divided into two phases or may be sub-divided into more than three phases.

Once the classification section 330 classifies the phases of the MAP, the phase model applier 340 may estimate blood pressure by applying a blood pressure estimation model corresponding to each of the classified phases of the MAP, among blood pressure estimation models defined for each phase. The blood pressure estimation models for each phase may be generated using DNN-based deep learning as described above, and may be a model for estimating SBP for each phase. The phase model applier 340 may input the feature, extracted by the feature extractor 310, and/or the initial SBP, obtained by the initial model applier 320, to the blood pressure estimation model for a corresponding phase of the MAP, and the blood pressure estimation model for the phase of the MAP may output a final SBP as a result.

The processor 300 may output a final SBP and a final DBP by using the SBP obtained by the phase model applier 340, and by using the initial DBP as it is, which is obtained by the initial model applier 320 or converting the initial DBP using a predetermined conversion equation.

Figure 5:
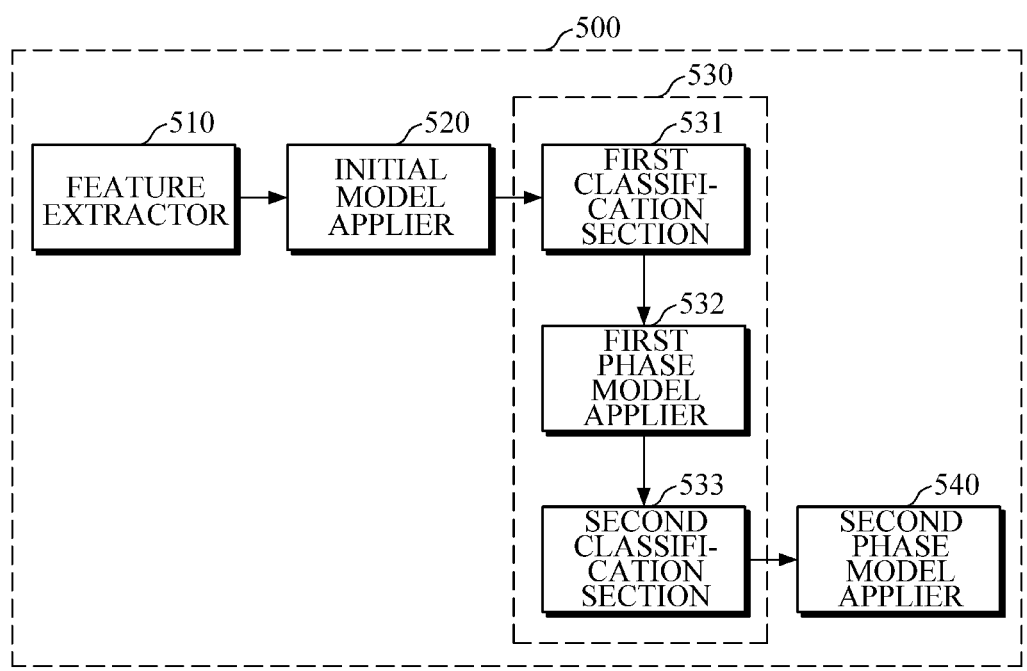
FIG. 5 is a diagram illustrating another example of a configuration of a processor of FIGS. 1 and 2.

FIG. 5 is a diagram illustrating another example of a configuration of a processor of FIGS. 1 and 2.

Referring to FIG. 5, a processor 500 according to an example embodiment includes a feature extractor 510, an initial model applier 520, a classification section 530, and a second phase model applier 540.

As described above, the feature extractor 510 may extract a feature based on the pulse wave signal and/or the contact force/pressure. Further, the feature extractor 510 may extract user characteristic information as features from the storage 210.

The initial model applier 520 may obtain an initial SBP and/or an initial DBP by applying an initial estimation model to the feature extracted by the feature extractor 510. The initial estimation model may be based on DNN, and may include an SBP estimation model and a DBP estimation model.

The classification section 530 may include a first classification section 531, a first phase model applier 532, and a second classification section 533. In this embodiment, the classification section 530 may perform two-stage classification of MAP, thereby further improving accuracy.

The first classification section 531 may obtain a first MAP based on the initial SBP and the initial DBP which are obtained by the initial model applier 520. Further, the first classification section 531 may classify phases of the first MAP according to a first classification criterion based on magnitudes of the first MAP. For example, if a magnitude of the first MAP is greater than or equal to a first value (e.g., 95), the first classification section 531 may classify the first MAP as a first phase, if a magnitude of the first MAP is less than the first value but greater than a second value (e.g., 80), the first classification section 531 may classify the first MAP as a second phase, and if a magnitude of the first MAP is less than or equal to the second value, the first classification section 531 may classify the first MAP as a third phase. In this case, a number of phases is not particularly limited, and the first value, the second value, etc., may be pre-obtained by training.

The first phase model applier 532 may obtain a first SBP by applying a first estimation model corresponding to each of the phases of the first MAP which are classified by the first classification section 531. In this case, the first estimation model for each phase may use the feature, extracted by the feature extractor 510, and the initial SBP, obtained by the initial model applier 520, as an input and may use the first SBP as an output. The first estimation model for each phase may be defined as a DNN model for each of the first phase, the second phase, and the third phase, and may be generated by being trained based on deep learning and the like.

The second classification section 533 may obtain a second MAP based on the initial DBP, obtained by the initial model applier 520, and the first SBP obtained by the first phase model applier 532. Further, the second classification section 533 may classify phases of the second MAP according to a second classification criterion. For example, if a magnitude of the second MAP is greater than or equal to a third value (e.g., 95), the second classification section 533 may classify the second MAP as a first phase, if a magnitude of the second MAP is less than the third value but greater than a fourth value (e.g., 80), the second classification section 533 may classify the second MAP as a second phase, and if a magnitude of the second MAP is less than or equal to the fourth value, the second classification section 533 may classify the second MAP as a third phase. A number of phases is not particularly limited, and the third value, the fourth value, etc., may be pre-obtained by training. The third value and the fourth value may be equal to the first value and the second value, respectively, but the values are not limited thereto.

The second phase model applier 540 may obtain a second SBP by applying a second estimation model corresponding to each of the phases of the second MAP which are classified by the second classification section 533. In this case, the second estimation model for each phase may use the feature, extracted by the feature extractor 510, and the first SBP, obtained by the first phase model applier 532, as an input and the second SBP as an output. As described above, the second estimation model for each phase may be defined as a DNN model for each of the first phase, the second phase, and the third phase, and may be generated by being trained based on deep learning and the like.

The processor 500 may output a final SBP and a final DBP by using the second SBP obtained by the second phase model applier 540, and by using the initial DBP as it is, which is obtained by the initial model applier 520 or converting the initial DBP using a predetermined conversion equation.

Figure 6:
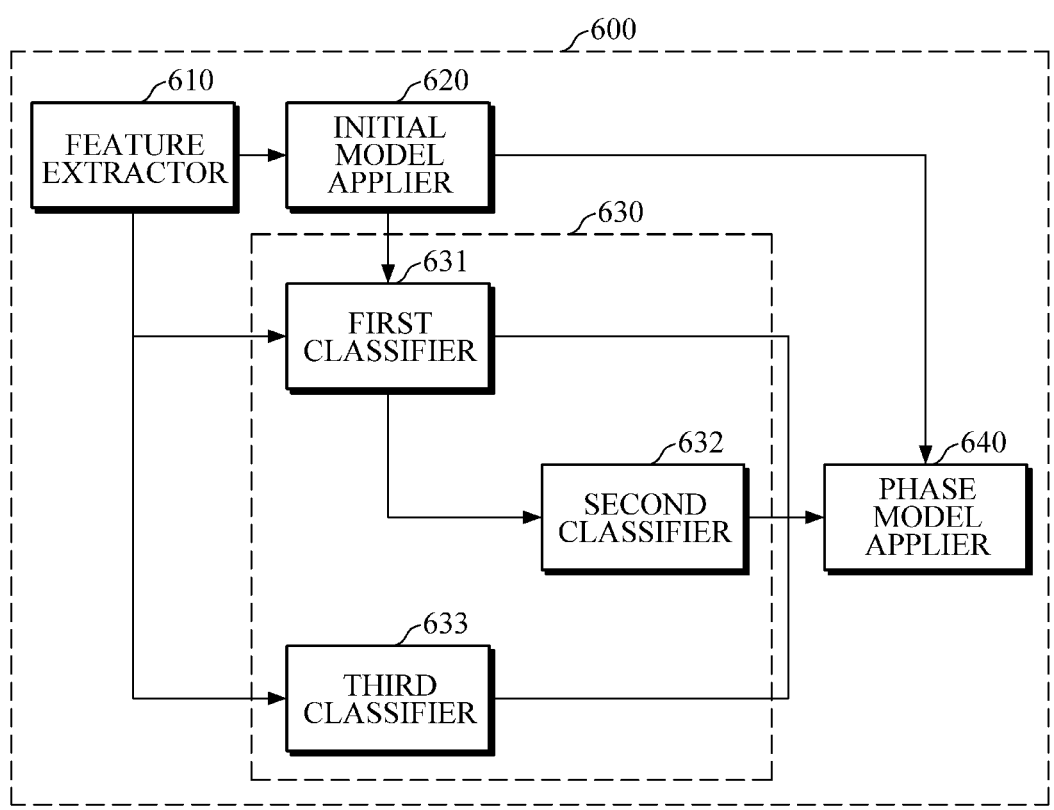
FIG. 6 is a diagram illustrating yet another example of a configuration of a processor of FIGS. 1 and 2.

FIG. 6 is a diagram illustrating yet another example of a configuration of a processor of FIGS. 1 and 2.

Referring to FIG. 6, a processor 600 according to an embodiment includes a feature extractor 610, an initial model applier 620, a classification section 630, and a phase model applier 640.

As described above, the feature extractor 610 may extract features based on the pulse wave signal and/or the contact force/pressure. Further, the feature extractor 610 may extract user characteristic information as features from the storage 210.

The initial model applier 620 may obtain an initial SBP and/or an initial DBP by applying an initial estimation model to the features extracted by the feature extractor 610. The initial estimation model may be based on DNN, and may include an SBP estimation model and a DBP estimation model.

The classification section 630 may classify phases of an estimated MAP, which is estimated based on the pulse wave signal, by using two or more classifiers 631, 632, and 633. For example, the classifiers 631, 632, and 633 may classify the estimated MAP into a first phase indicating that the estimated MAP is "high", a second phase indicating that the estimated MAP is "medium", and a third phase indicating that the estimated MAP is "low". The first classifier 631, the second classifier 632, and the third classifier 633 may be trained using mini-batch balancing, with a mini-batch of training data containing a relatively larger number of the estimated MAP values classified as being "high" than the estimated MAP values classified as not being "high".

The classification section 630 may input the feature, extracted by the feature extractor 610, into the first classifier 631 to classify whether the estimated MAP belongs to the first phase. Once the feature is input, the first classifier 631 may output a first probability value to determine whether the estimated MAP belongs to the first phase. If the first probability value exceeds a first threshold value (e.g., 0.53), the classification section 630 may classify the estimated MAP as the first phase.

If the first probability value is less than or equal to the first threshold value, the classification section 630 may use the second classifier 632 to reclassify whether the estimated MAP is "high" or not. For example, once the feature is input, the second classifier 632 may output a second probability value (e.g., 0.74). In this case, the second classifier 632 may be trained using a mini-batch of training data containing a relatively large number of "high" estimated MAP values, e.g., containing the estimated MAP values classified as being "high" to the estimated MAP values classified as not being "high" at a ratio of 1:0.7. If the second probability value exceeds a second threshold value, the classification section 630 may reclassify the estimated MAP value as the first phase.

In addition, the classification section 630 may input the extracted feature into the third classifier 633, and may classify whether the estimated MAP belongs to the third phase or not based on a third probability value output by the third classifier 633. For example, if the third probability value exceeds a third threshold value (e.g., 0.74), the classification section 630 may classify the estimated MAP as the third phase. Upon classification by the third classifier 633, if the estimated MAP is not classified as the third phase, and at the same time is not classified as the first phase upon classification by the second classifier 632, the classification section 630 may classify the estimated MAP as the second phase.

The phase model applier 640 may estimate SBP by applying a phase estimation model, corresponding to the classified phase of the estimated MAP, based on the classification result of the classification section 630. In this case, the phase model applier 640 may input the initial SBP, obtained by the initial model applier 620, and/or the feature, extracted by the feature extractor 610, to the phase estimation model, and may obtain an output of the phase estimation model as the SBP.

The processor 600 may provide a user with the SBP, obtained by the phase model applier 640, and the DBP, obtained by the initial model applier 620, as a final SBP and a final DBP.

Figure 7:
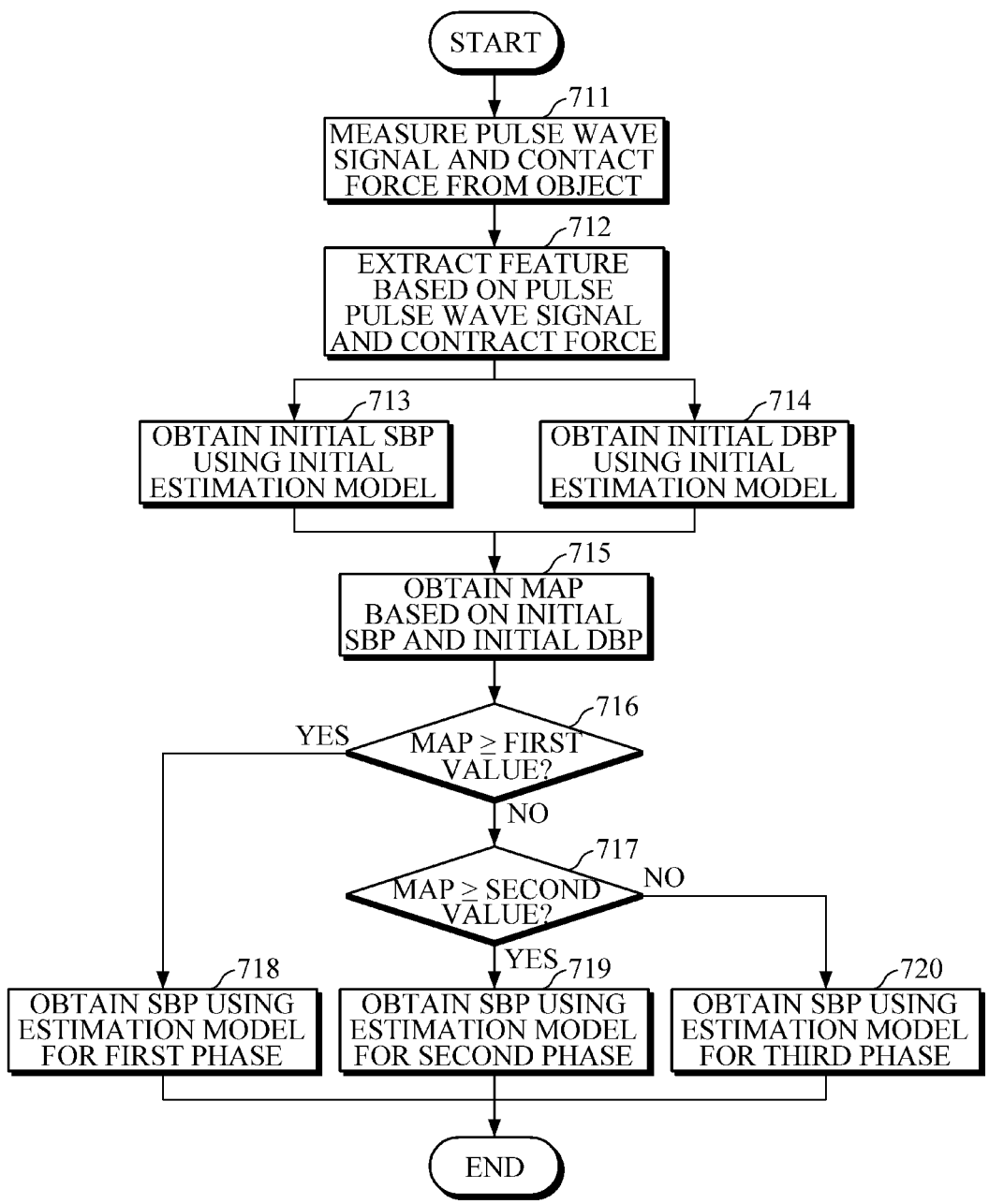
FIG. 7 is a flowchart illustrating a method of estimating blood pressure according to an example embodiment of the disclosure.

FIG. 7 is a flowchart illustrating a method of estimating blood pressure according to an example embodiment of the disclosure.

The method of FIG. 7 is an example of a method of estimating blood pressure, which is performed by the apparatus for estimating blood pressure according to any of the embodiments of FIGS. 1 and 2, and the method will be briefly described below to avoid redundancy.

The apparatus for estimating blood pressure may measure a pulse wave signal and/or a contact force/pressure from an object in 711.

Then, the apparatus for estimating blood pressure may extract a feature based on the pulse wave signal and/or the contract force/pressure in 712. In this case, the feature may include amplitude and/or time values at a maximum point of the pulse wave, time and amplitude values of constituent pulse waveform components related to propagation and reflection waves, an area of a predetermined period of a waveform of the pulse wave signal, an amplitude value MA at a maximum point of the pulse wave, a contact pressure value MP at the maximum point of the pulse wave, a contact pressure value DP at a point corresponding to an amplitude value which is a first percentage of the amplitude value MA at the maximum point, a contact pressure value SP at a point corresponding to an amplitude value which is a second percentage of the amplitude value MA at the maximum point, a width between points corresponding to a predetermined percentage of an interval between an onset point and a maximum point of the pulse wave in the oscillometric waveform envelope OW, a user's age, gender, health condition, and the like.

Subsequently, the apparatus for estimating blood pressure may obtain an initial SBP and an initial DBP by using an initial estimation model in 713 and 714, and may obtain MAP based on the initial SBP and the initial DBP in 715.

Next, if the obtained MAP is greater than or equal to a first value, the apparatus for estimating blood pressure may classify the MAP as a first phase in 716, and may obtain SBP by using an estimation model for the first phase in 718. If it is determined in 716 that the obtained MAP is less than the first value, the apparatus for estimating blood pressure may determine whether the MAP is greater than a second value in 717, and if the MAP is greater than the second value, the apparatus for estimating blood pressure may classify the MAP as a second phase and may obtain SBP by using an estimation model for the second phase in 719. If the MAP is less than or equal to the second value in 717, the apparatus for estimating blood pressure may classify the MAP as a third phase and may obtain SBP by using an estimation model for the third phase in 720.

Figure 8:
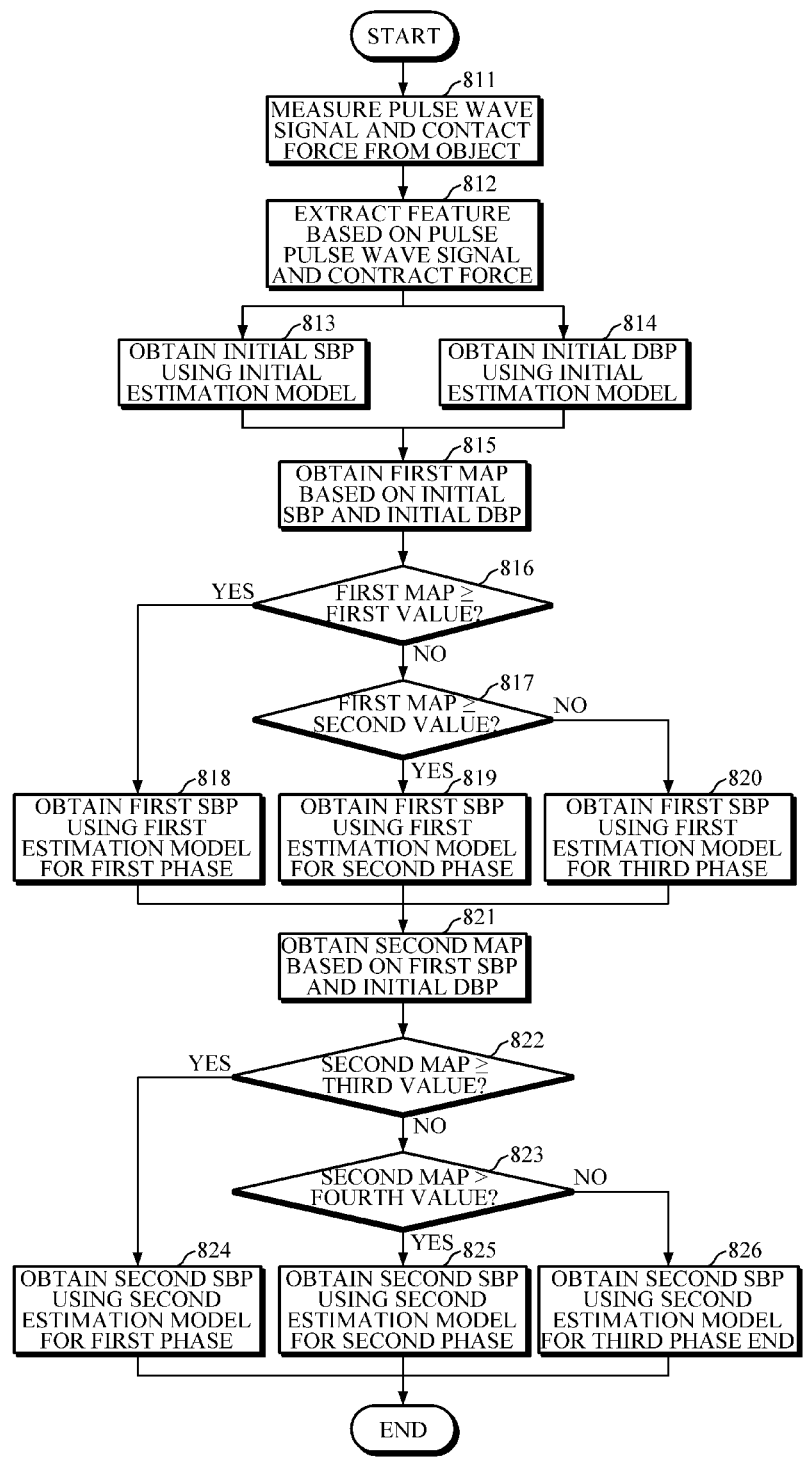
FIG. 8 is a flowchart illustrating a method of estimating blood pressure according to another example embodiment of the disclosure.

FIG. 8 is a flowchart illustrating a method of estimating blood pressure according to another example embodiment of the disclosure.

The method of FIG. 8 is another example of a method of estimating blood pressure, which is performed by the apparatus for estimating blood pressure according to any of the embodiments of FIGS. 1 and 2, and the method will be briefly described below to avoid redundancy.

The apparatus for estimating blood pressure may measure a pulse wave signal and/or a contact force/pressure from an object in 811, and may extract a feature based on the pulse wave signal and/or the contract force/pressure in 812.

Then, the apparatus for estimating blood pressure may obtain an initial SBP and an initial DBP by using an initial estimation model in 813 and 814, and may obtain a first MAP based on the initial SBP and the initial DBP in 815.

Subsequently, if the obtained first MAP is greater than or equal to a first value, the apparatus for estimating blood pressure may classify the first MAP as a first phase in 816, and may obtain a first SBP by using a first estimation model for the first phase in 818. If it is determined in 816 that the first MAP is less than the first value, the apparatus for estimating blood pressure may determine whether the first MAP is greater than a second value in 817, and if the first MAP is greater than the second value, the apparatus for estimating blood pressure may classify the first MAP as a second phase and may obtain a first SBP by using a first estimation model for the second phase in 819. If the first MAP is less than or equal to the second value in 817, the apparatus for estimating blood pressure may classify the first MAP as a third phase and may obtain a first SBP by using a first estimation model for the third phase in 820.

Next, the apparatus for estimating blood pressure may obtain a second MAP based on the first SBP and the initial DBP in 821.

Then, if the obtained second MAP is greater than or equal to a third value, the apparatus for estimating blood pressure may classify the second MAP as a first phase in 822 and may obtain a second SBP by using a second estimation model for the first phase in 824. If it is determined in 822 that the second MAP is less than the third value, the apparatus for estimating blood pressure may determine whether the second MAP is greater than a fourth value in 823, and if the second MAP is greater than the fourth value, the apparatus for estimating blood pressure may classify the second MAP as a second phase and may obtain a second SBP by using a second estimation model for the second phase in 825. If the second MAP is less than or equal to the fourth value, the apparatus for estimating blood pressure may classify the second MAP as a third phase and may obtain a second SBP by using a second estimation model for the third phase in 826.

Figure 9:
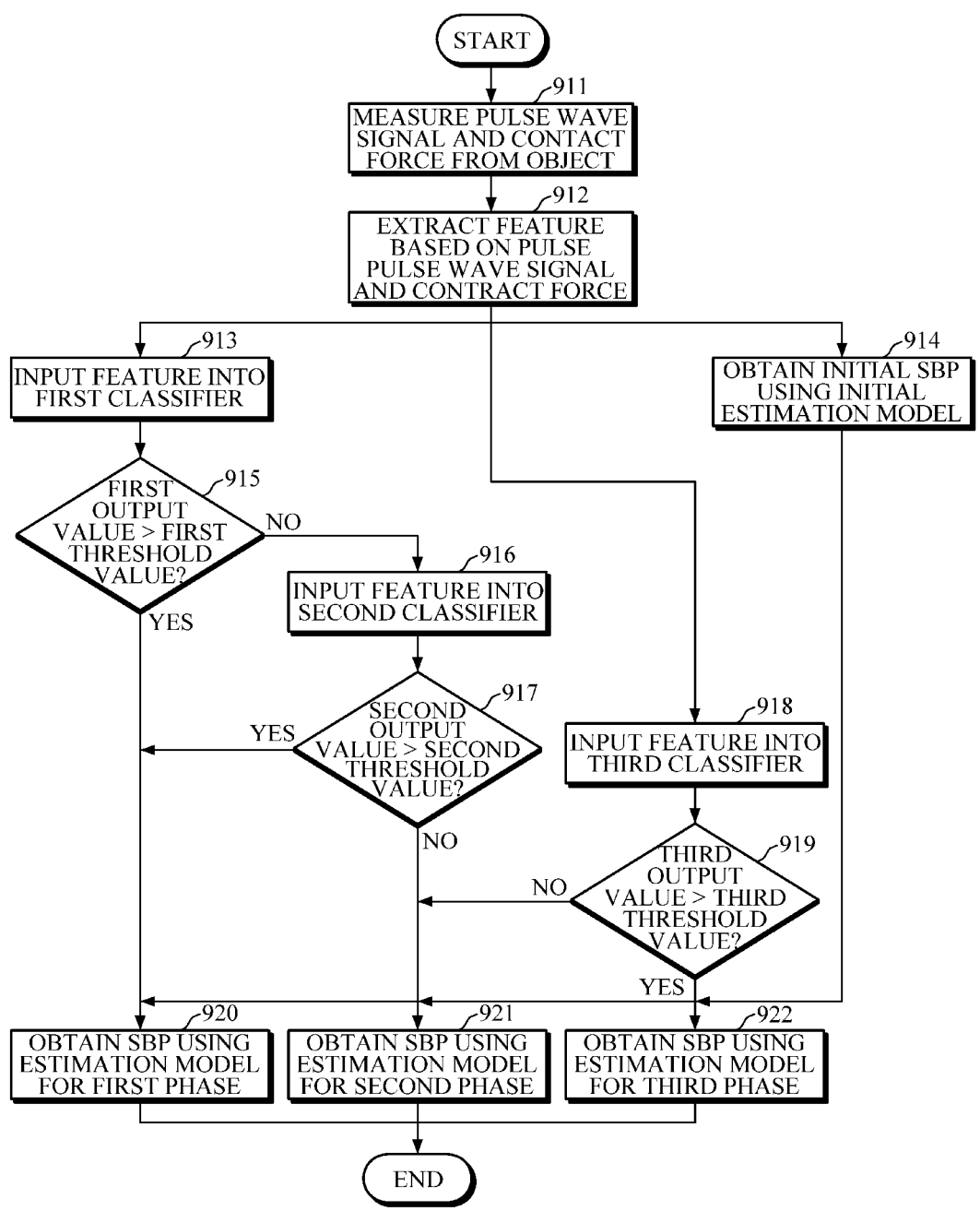
FIG. 9 is a flowchart illustrating a method of estimating blood pressure according to yet another example embodiment of the disclosure.

FIG. 9 is a flowchart illustrating a method of estimating blood pressure according to yet another example embodiment of the disclosure.

The method of FIG. 9 is yet another example of a method of estimating blood pressure, which is performed by the apparatus for estimating blood pressure according to any of the embodiments of FIGS. 1 and 2, and the method will be briefly described below to avoid redundancy.

The apparatus for estimating blood pressure may measure a pulse wave signal and/or a contact force/pressure from an object in 911, and may extract features based on the pulse wave signal and/or the contract force/pressure in 912.

Then, the apparatus for estimating blood pressure may input the feature into a first classifier in 913, and may obtain an initial SBP by using an initial estimation model in 914.

Subsequently, if a first output value of the first classifier is greater than a first threshold value in 915, the apparatus for estimating blood pressure may classify the feature as a first phase, and may obtain SBP by using an estimation model for the first phase in 920. In this case, the feature extracted in 912 and the initial SBP obtained in 914 may be input to the estimation model for the first phase.

Next, if the first output value of the first classifier is not greater than the first threshold value, the apparatus for estimating blood pressure may input the feature into a second classifier in 916, and if a second output value of the second classifier is greater than a second threshold value in 917, the apparatus for estimating blood pressure may reclassify the feature as the first phase and may obtain SBP by using the estimation model for the first phase in 920.

Then, the apparatus for estimating blood pressure may input the feature into a third classifier in 918, and if a third output value of the third classifier is greater than a third threshold value in 919, the apparatus for estimating blood pressure may classify the feature as a third phase and may obtain SBP by using an estimation model for the third phase in 922.

If the second output value is not greater than the second threshold value in 917 and the third output value is less than or equal to the third threshold value in 919, the apparatus for estimating blood pressure may classify the feature as a second phase and may obtain SBP by using an estimation model for the second phase in 921.

Figure 10:
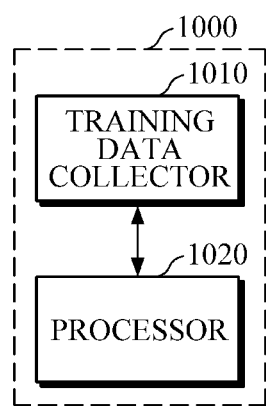
FIG. 10 is a block diagram illustrating an apparatus for estimating blood pressure according to yet another example embodiment of the disclosure.

FIG. 10 is a block diagram illustrating an apparatus for estimating blood pressure according to yet another example embodiment of the disclosure.

Referring to FIG. 10, an apparatus 1000 for estimating blood pressure according to yet another embodiment includes a training data collector 1010 and a processor 1020.

The training data collector 1010 may collect, from a plurality of users, a plurality of pulse wave signals, a plurality of contact force/pressure values, user characteristic information, features extracted based on the pulse wave signals and/or contact force/pressure values, a reference blood pressure of each user, i.e., a reference MAP, a reference SBP, and a reference DBP, as training data.

The training data collector 1010 may include a sensor for measuring pulse wave signals and contact force/pressure from users. Once the sensor measures the pulse wave signals and/or contact force/pressure from the users, the training data collector 1010 may extract features based on each of the pulse wave signals and/or contact force/pressure.

The training data collector 1010 may receive a reference blood pressure from, e.g., a cuff-type blood pressure measuring device and the like through a communicator. Further, the training data collector 1010 may receive user characteristic information from a user's smartphone and the like, or may display an interface on a display through an outputter and may receive input of user characteristic information from a user through the interface.

The processor 1020 may train a classifier and a blood pressure estimation model based on the collected training data.

Figure 11:
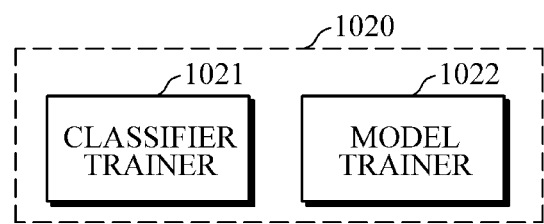
FIG. 11 is a diagram illustrating an example of a configuration of a processor of FIG. 10.

FIG. 11 is a diagram illustrating an example of a configuration of a processor of FIG. 10.

Referring to FIG. 11, a processor 1020 includes a classifier trainer 1021 and a model trainer 1022.

The classifier trainer 1021 may train a plurality of classifiers applied to the aforementioned embodiment of FIG. 6. For example, the classifier trainer 1021 may train a first classifier, a second classifier, and a third classifier to classify MAP into different phases by using training data as an input. In this case, the classifier trainer 1021 may train the classifiers using mini-batch balancing, with a mini-batch containing a relatively large number of features having a "high" reference MAP, so that the first classifier and the second classifier may classify the "high" MAP phase more effectively.

The classifier trainer 1021 may train the first classifier, the second classifier, and the third classifier using a reference MAP as ground truth data and the features as input data. The first classifier serves to classify whether an estimated MAP is "high" or not, and may output a first probability value indicating that the estimated MAP is "high". The second classifier serves to reclassify whether an estimated MAP, which has been determined to be not "high" by the first classifier, is "high" or not, and may output a second probability value indicating that the estimated MAP is "high". The third classifier serves to classify whether an estimated MAP is "low" or not, and may output a third probability value indicating that the estimated MAP is "low".

By adjusting threshold values for the probability values, output from the respective classifiers, within a predetermined range, the classifier trainer 1021 may determine a threshold value having a highest accuracy. Further, the classifier trainer 1021 may train the classifiers by using a plurality of features individually, and may determine a feature, exhibiting excellent performance as a result of the training, to be a feature to be extracted from the pulse wave signal in the above embodiments.

The model trainer 1022 may train an estimation model for each phase described in the above embodiments. The estimation model for each phase may be trained using a reference SBP as ground truth data, and using the features and/or the obtained SBP values as input data. The estimation model may be defined for each phase and may be a deep neural network (DNN)-based model. The model trainer 1022 may train the estimation model for each phase based on deep learning, and may determine phase classification criteria, e.g., the first value, the second value, the third value, and the fourth value which are described above.

Figure 12:
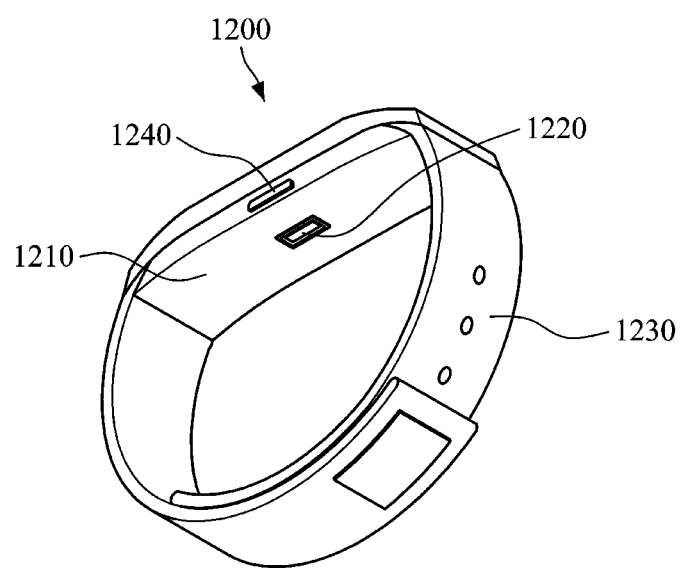
FIG. 12 is a diagram illustrating a wearable device according to an example embodiment of the disclosure.

FIG. 12 is a diagram illustrating a wearable device according to an example embodiment of the disclosure. One or more of various embodiments of the aforementioned apparatuses 100, 200, and 1000 for estimating bin-information may be mounted in the wearable device.

Referring to FIG. 12, the wearable device 1200 includes a main body 1210 and a strap 1230.

The strap 1230, which is connected to both ends of the main body 1210, may be flexible so as to be bent around a user's wrist. The strap 1230 may include a first strap and a second strap which are separated from each other. One ends of the first strap and the second strap are connected to the main body 1210, and the other ends thereof may be connected to each other via a connecting element. In this case, the connecting element may be formed as magnetic connection, Velcro connection, pin connection, and the like, but is not limited thereto. Further, the strap 1230 is not limited thereto, and may be integrally formed as a non-detachable band.

Air may be injected into the strap 1230, or the strap 1230 may be provided with an air bladder to have elasticity according to a change in pressure applied to the wrist, and may transmit the change in pressure of the wrist to the main body 1210.

A battery may be embedded in the main body 1210 or the strap 1230 to supply power to the wearable device 1200.

The main body 1210 may include a sensor 1220 mounted on one side thereof. The sensor 1220 may include a pulse wave sensor for measuring pulse wave signals. In addition, the sensor 1220 may further include a force/pressure sensor for measuring force/pressure between the wrist or finger and the sensor 1220.

A processor may be mounted in the main body 1210. The processor may be electrically connected to modules mounted in the wearable device 1200. The processor may estimate blood pressure based on the pulse wave signal and the contact force/pressure, which are measured by the sensor 1220. The processor may estimate blood pressure by using a blood pressure estimation model, which is defined for each of a plurality of phases classified according to magnitudes of MAP.

Further, the main body 1210 may include a storage which stores reference information for estimating blood pressure and performing various functions of the wearable device 1200, and information processed by various modules thereof.

In addition, the main body 1210 may include a manipulator 1240 which is provided on one side surface of the main body 1210, and receives a user's control command and transmits the received control command to the processor. The manipulator 1240 may have a power button to input a command to turn on/off the wearable device 1200.

Further, a display for outputting information to a user may be mounted on a front surface of the main body 1210. The display may have a touch screen for receiving a touch input. The display may receive a user's touch input and transmit the touch input to the processor, and may display processing results of the processor.

Moreover, the main body 1210 may include a communicator for communication with an external device. The communicator may transmit a blood pressure estimation result to the external device, e.g., a user's smartphone.

Figure 13:
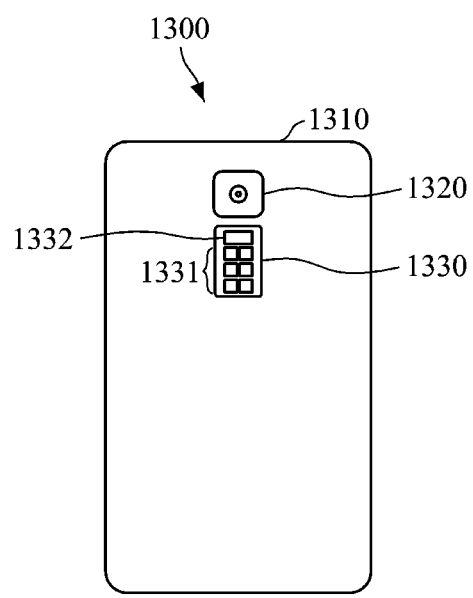
FIG. 13 is a diagram it g a smart device according to an example embodiment of the disclosure.

FIG. 13 is a diagram illustrating a smart device according to an example embodiment of the disclosure. The smart device may include a smartphone, a tablet PC, and the like.

The smart device may include functions of the aforementioned apparatuses 100, 200, and 1000 for estimating bioinformation.

Referring to FIG. 13, the smart device 1300 includes a main body 1310 and a pulse wave sensor 1330 mounted on one surface of the main body 1310. Further, a force/pressure sensor for measuring a contact force/pressure of a finger may be mounted in the main body 1310 at a lower end of the pulse wave sensor 1330.

Moreover, a display may be mounted on a front surface of the main body 1310. The display may visually output a blood pressure estimation result, a health condition evaluation result, and the like. The display may include a touch screen, and may receive information input through the touch screen and transmit the information to a processor.

The main body 1310 may include an image sensor 1320 as illustrated in FIG. 13. The image sensor 1320 may capture various images, and may acquire, for example, a fingerprint image of a finger being in contact with the pulse wave sensor 1330.

A processor may be mounted in the main body 1310 and may be electrically connected to various modules to control operations thereof. In response to a request for estimating blood pressure, the processor may control the pulse wave sensor and the force/pressure sensor, and may estimate blood pressure by using the pulse wave signal, the force/pressure, and a blood pressure estimation model defined for each phase.

The disclosure may be implemented as a computer-readable code written on a computer-readable recording medium. The computer-readable recording medium may be any type of recording device in which data is stored in a computer-readable manner.

Examples of the computer-readable recording medium include a ROM, a RAM, a CD-ROM, a magnetic tape, a floppy disc, an optical data storage, and a carrier wave (e.g., data transmission through the Internet). The computer-readable recording medium may be distributed over a plurality of computer systems connected to a network so that a computer-readable code is written thereto and executed therefrom in a decentralized manner. Functional programs, codes, and code segments needed for implementing the disclosure be readily deduced by programmers of ordinary skill in the art to which the disclosure pertains.

At least one of the components, elements, modules or units described herein may be embodied as various numbers of hardware, software and/or firmware structures that execute respective functions described above, according to an embodiment. For example, at least one of these components, elements or units may use a direct circuit structure, such as a memory, a processor, a logic circuit, a look-up table, etc. that may execute the respective functions through controls of one or more microprocessors or other control apparatuses. Also, at least one of these components, elements or units may be specifically embodied by a module, a program, or a part of code, which contains one or more executable instructions for performing specified logic functions, and executed by one or more microprocessors or other control apparatuses. Also, at least one of these components, elements or units may further include or implemented by a processor such as a central processing unit (CPU) that performs the respective functions, a microprocessor, or the like. Two or more of these components, elements or units may be combined into one single component, element or unit which performs all operations or functions of the combined two or more components, elements of units. Also, at least part of functions of at least one of these components, elements or units may be performed by another of these components, element or units. Further, although a bus is not illustrated in the block diagrams, communication between the components, elements or units may be performed through the bus. Functional aspects of the above embodiments may be implemented in algorithms that execute on one or more processors. Furthermore, the components, elements or units represented by a block or processing operations may employ any number of related art techniques for electronics configuration, signal processing and/or control, data processing and the like.

While the disclosure has been particularly shown and described with reference to embodiments thereof, it will be understood that various changes in form and details may be made therein without departing from the spirit and scope of the following claims.

What is claimed is:

1. An apparatus for estimating blood pressure, the apparatus comprising:
a pulse wave sensor configured to measure a pulse wave signal from an object; and
a processor configured to obtain a mean arterial pressure (MAP) based on the pulse wave signal,
wherein the processor is configured to:
extract a feature based on the pulse wave signal;
obtain an initial systolic blood pressure (SBP) and an initial diastolic blood pressure (DBP) from the extracted feature by using an initial estimation model;
obtain a first MAP based on the initial SBP and the initial DBP;
classify a phase of the first MAP according to a first classification criterion;
obtain a first SBP by using a first estimation model corresponding to the phase of the first MAP among first estimation models for respective phases of the first MAP;
obtain a second MAP based on the first SBP and the initial DBP;
classify a phase of the second MAP according to a second classification criterion;
obtain a second SBP by using a second estimation model corresponding to the phase of the second MAP among second estimation models for respective phases of the second MAP; and
output a final SBP and a final DBP by using the second SBP and the initial DBP.

2. The apparatus of claim 1, wherein the first and second estimation models are trained based on deep learning, including a Deep Neural Network (DNN), and generated for the classified phase of the first MAP that is defined based on a magnitude of the first MAP and the classified phase of the second MAP that is defined based on a magnitude of the second MAP.

3. The apparatus of claim 1, further comprising a force sensor configured to measure a contact force applied by the object to the pulse wave sensor, and
wherein the processor is further configured to obtain an oscillometric waveform envelope based on the pulse wave signal and the contact force, and extract the feature based on the obtained oscillometric waveform envelope.

4. The apparatus of claim 3, wherein the processor is further configured to extract as the feature, from the oscillometric waveform envelope, one or more of a maximum amplitude value, a contact pressure value at a maximum amplitude point, a width between points corresponding to a predetermined percentage of the maximum amplitude value, and a contact pressure value at a point corresponding to an amplitude value which is the predetermined percentage of the maximum amplitude value.

5. An apparatus for estimating blood pressure, the apparatus comprising:
   a pulse wave sensor configured to measure a pulse wave signal from an object; and
   a processor configured to:
      extract a feature based on the pulse wave signal;
      input the extracted feature into a first classifier, and in response to an output value of the first classifier exceeding a first threshold value, classify a mean arterial pressure (MAP) as a first phase;
      in response to the output value of the first classifier being less than or equal to the first threshold value, input the extracted feature into a second classifier, and in response to an output value of the second classifier exceeding a second threshold value, classify the MAP as the first phase;
      obtain a systolic blood pressure (SBP) by using an estimation model corresponding to the classified phase of the MAP among estimation models corresponding to respective phases of the MAP.

6. The apparatus of claim 5, wherein the processor is further configured to input the extracted feature into a third classifier, and in response to an output value of the third classifier exceeding a third threshold value, classify the MAP as a third phase, and in response to the output value of the second classifier being less than or equal to the second threshold value and the output value of the third classifier being less than or equal to the third threshold value, classify the MAP as a second phase.

7. The apparatus of claim 5, wherein the processor is further configured to obtain an initial SBP from the extracted feature by using an initial estimation model, and obtain the SBP by inputting the extracted feature and the initial SBP to the estimation model.

8. A method of estimating blood pressure, the method comprising:
   measuring a pulse wave signal from an object using a pulse wave sensor;
   extracting a feature based on the pulse wave signal;
   obtaining an initial systolic blood pressure (SBP) and an initial diastolic blood pressure (DBP) from the extracted feature by using an initial estimation model;
   obtaining a first mean arterial pressure (MAP) based on the initial SBP and the initial DBP;
   classifying a phase of the first MAP according to a first classification criterion;
   obtaining a first SBP by using a first estimation model corresponding to the phase of the first MAP among first estimation models for respective phases of the first MAP;
   obtaining a second MAP based on the first SBP and the initial DBP; and
   classifying a phase of the second MAP according to a second classification criterion;
   obtaining a second SBP by using a second estimation model corresponding to the phase of the second MAP among second estimation models for respective phases of the second MAP.

9. The method of claim 8, further comprising measuring a contact force applied by the object to the pulse wave sensor by a force sensor,
   wherein the extracting comprises obtaining an oscillometric waveform envelope based on the pulse wave signal and the contact force, and extracting the feature based on the obtained oscillometric waveform envelope.

10. The method of claim 8, further comprising outputting a final SBP and a final DBP by using the second SBP and the initial DBP.

* * * * *